(12) United States Patent
Edwards et al.

(10) Patent No.: US 9,814,421 B2
(45) Date of Patent: Nov. 14, 2017

(54) APPARATUS FOR DETERMINING LIFTING CAPACITY

(71) Applicant: BARDAVON HEALTH INNOVATIONS, LLC, Overland Park, KS (US)

(72) Inventors: Douglas Wayne Edwards, Olathe, KS (US); Levi Kane Shaffer, Independence, KS (US)

(73) Assignee: Bardavon Health Innovations, LLC, Overland Park, KS (US)

( * ) Notice: Subject to any disclaimer, the term of this patent is extended or adjusted under 35 U.S.C. 154(b) by 253 days.

(21) Appl. No.: 14/954,428

(22) Filed: Nov. 30, 2015

(65) Prior Publication Data

US 2017/0150915 A1 Jun. 1, 2017

(51) Int. Cl.
*A61B 5/22* (2006.01)

(52) U.S. Cl.
CPC .............. *A61B 5/224* (2013.01); *A61B 5/221* (2013.01)

(58) Field of Classification Search
CPC ..................................... A61B 5/224
See application file for complete search history.

(56) References Cited

U.S. PATENT DOCUMENTS

| | | | |
|---|---|---|---|
| 5,898,111 A | 4/1999 | Blankenship et al. | |
| 6,033,412 A * | 3/2000 | Losken | A61B 17/663 606/105 |
| 6,387,022 B1 | 5/2002 | Smith | |
| 7,011,611 B1 | 3/2006 | Ripley | |
| 7,491,157 B1 | 2/2009 | Lin | |
| 7,785,240 B2 | 8/2010 | Stugart | |
| 8,012,069 B2 | 9/2011 | Towley, III et al. | |
| 8,382,647 B1 | 2/2013 | Hodes et al. | |
| 8,454,485 B1 | 6/2013 | Hodes et al. | |
| 8,568,280 B2 | 10/2013 | Mendoza | |
| 8,591,384 B2 | 11/2013 | Marji | |
| 8,668,630 B2 | 3/2014 | Towley, III et al. | |
| 8,684,889 B1 | 4/2014 | Berrisford | |
| 8,834,330 B1 * | 9/2014 | Morales | A63B 21/0605 482/107 |
| 8,858,406 B2 | 10/2014 | Klukas | |
| 9,011,300 B2 | 4/2015 | Hodes et al. | |
| 9,022,906 B1 | 5/2015 | Nelson | |
| 2003/0216716 A1 * | 11/2003 | Desarzens | A61B 17/1666 606/1 |
| 2006/0091622 A1 * | 5/2006 | Sabol | A63C 10/14 280/14.24 |
| 2009/0075792 A1 | 3/2009 | Stugart | |
| 2013/0267393 A1 | 10/2013 | Hodes et al. | |
| 2014/0274597 A1 | 9/2014 | Towley, III | |
| 2015/0051053 A1 | 2/2015 | Conen | |

(Continued)

*Primary Examiner* — Clayton E Laballe
*Assistant Examiner* — Dennis Hancock
(74) *Attorney, Agent, or Firm* — Lathrop Gage LLP

(57) ABSTRACT

Apparatus for measuring lifting capacity are described. An apparatus for measuring lifting capacity has a container having an open top, opposed parallel side walls, a front wall, a back wall, and a base extending between the walls which defines an open space between the walls; and a handle removably attached to the base. The handle includes a bottom plate; a rod that extends vertically from the bottom plate, and a grip portion that is configured to connect to a locking means formed in a top portion of the rod.

19 Claims, 25 Drawing Sheets

(56) References Cited

U.S. PATENT DOCUMENTS

| | | |
|---|---|---|
| 2015/0174445 A1 | 6/2015 | Robertson, Jr. |
| 2015/0182777 A1 | 7/2015 | Rarity, IV |
| 2016/0263421 A1* | 9/2016 | Gvoich .............. A63B 21/0605 |
| 2017/0065845 A1* | 3/2017 | Pinkus ............... A63B 21/0552 |

* cited by examiner

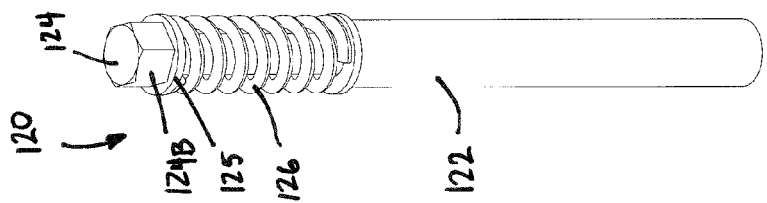
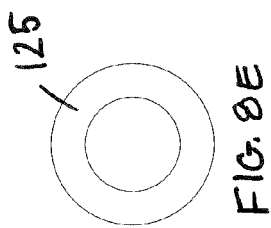
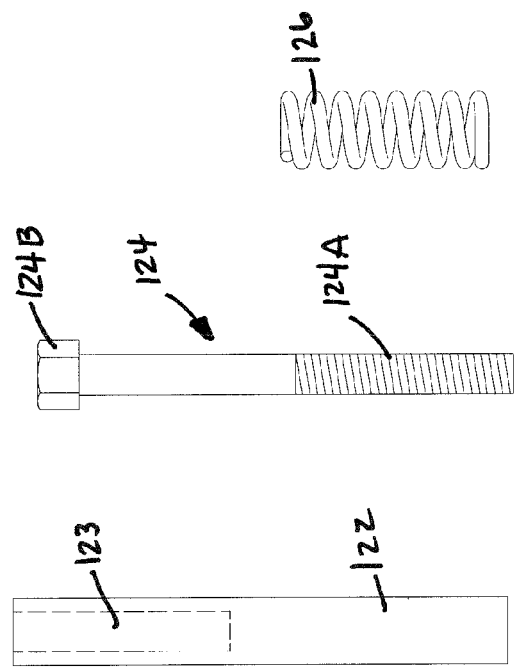
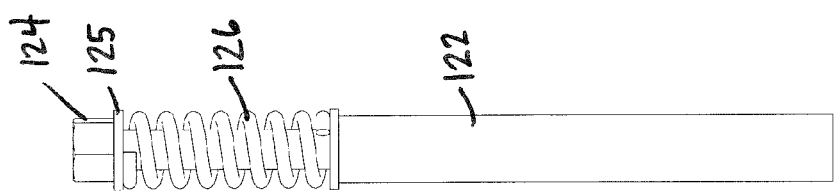

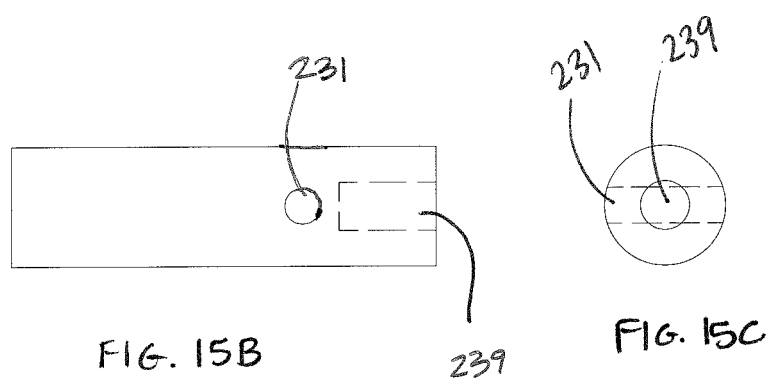

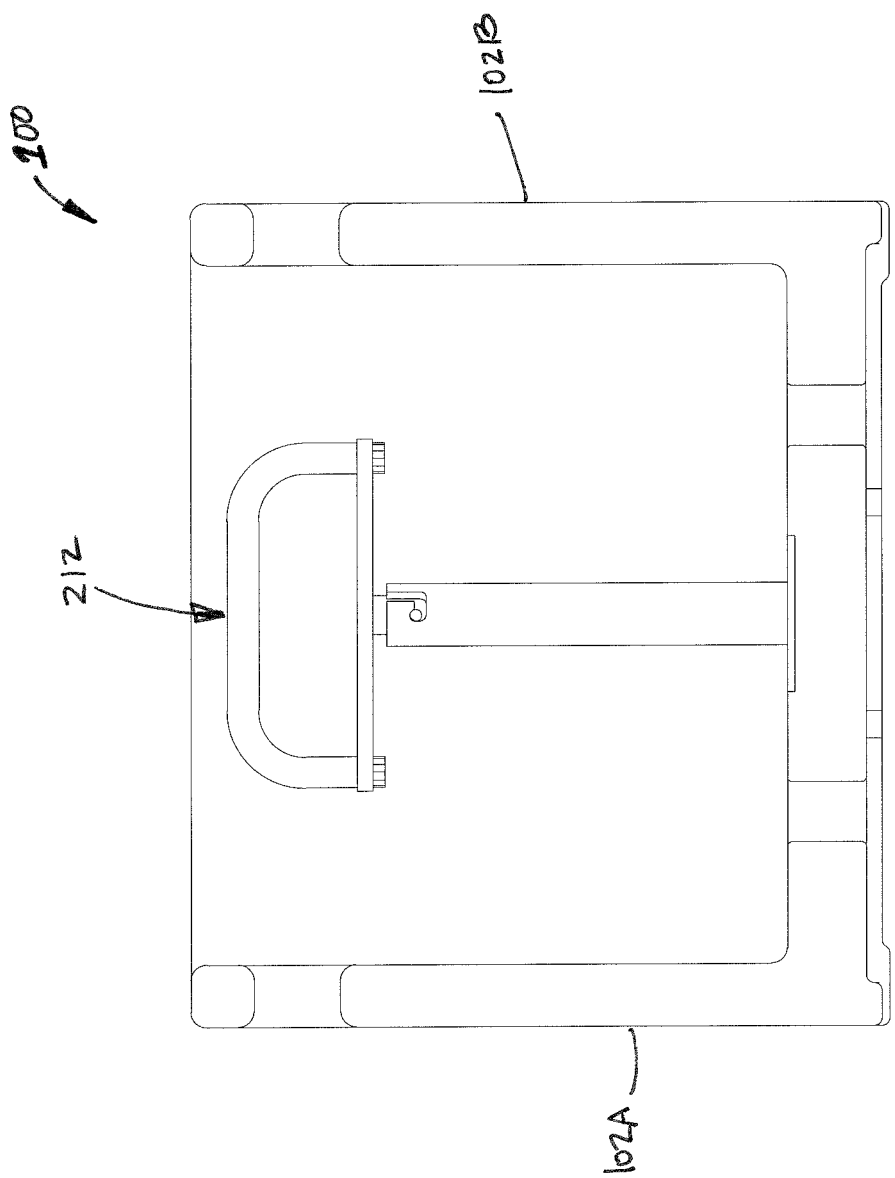

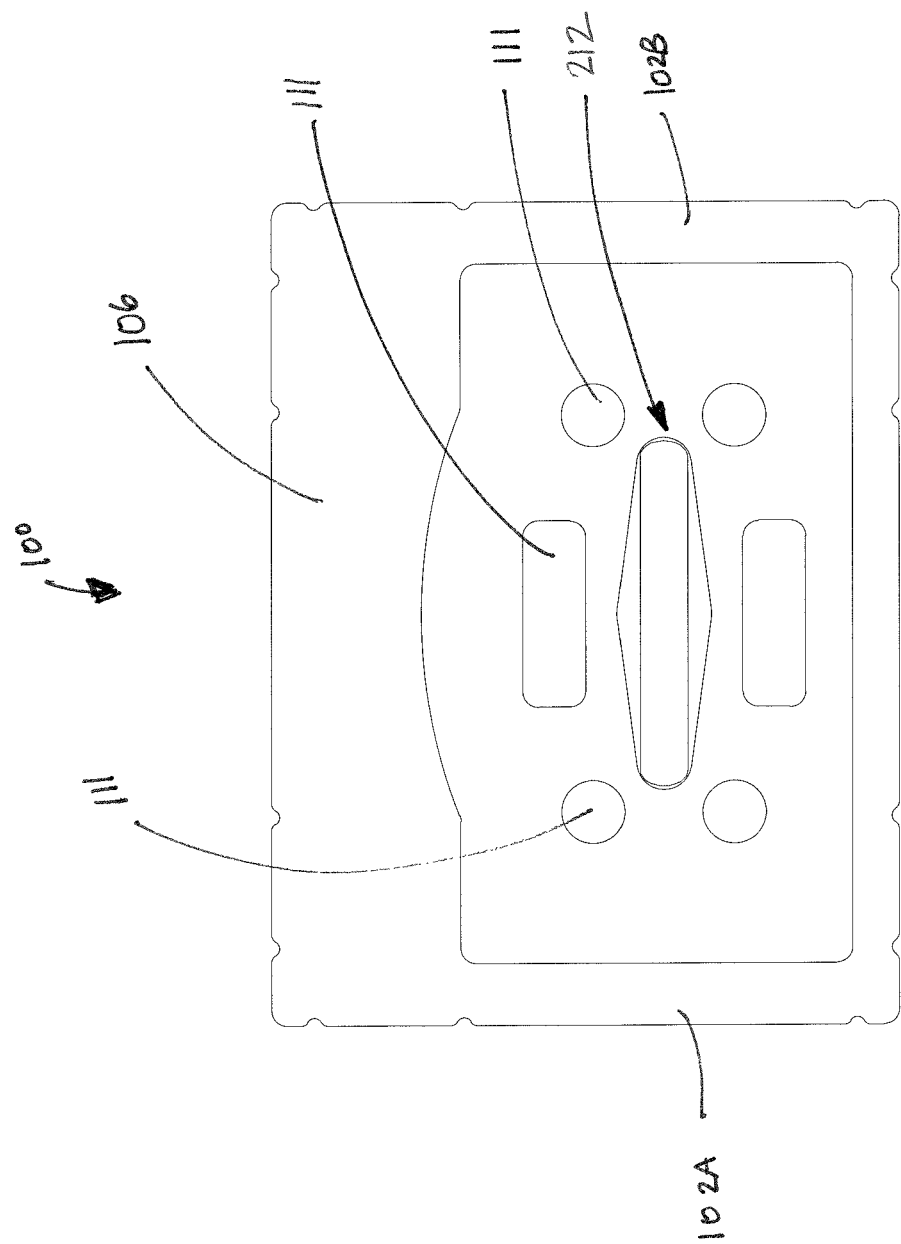

APPARATUS FOR DETERMINING LIFTING CAPACITY

BACKGROUND

The present invention relates to apparatus for measuring lifting capacity. There are many situations in which it may be desirable to evaluate the physical performance of a person, and in particular a person's lifting capacity. Many tests have been developed that provide a baseline indication of the person's lifting capacity. However, it is often difficult to tell whether the person is expending maximum effort during the evaluation, and in fact, the person may be intentionally attempting to skew the results. For example, a person being evaluated as part of a workman's compensation claim may unfortunately be motivated to not perform to the best of his or her ability. Conversely, there may be times that the person is providing maximum effort and the testing clinician may skew the results. For example, during an evaluation of a person for workman's compensation claim, the person may actually be expending maximum effort but the testing clinician makes subjective observations that the person is not expending maximum effort. Accordingly, apparatus for objectively measuring a person's lifting capacity which may provide a more accurate representation of the person's lifting capacity are desirable.

SUMMARY

The following presents a simplified summary of the invention in order to provide a basic understanding of some aspects of the invention. This summary is not an extensive overview of the invention. It is not intended to identify critical elements of the invention or to delineate the scope of the invention. Its sole purpose is to present some concepts of the invention in a simplified form as a prelude to the more detailed description that is presented elsewhere.

In one embodiment, an apparatus for measuring lifting capacity has a container having an open top, opposed parallel side walls, a front wall, a back wall, and a base extending between the walls which defines an open space between the walls; and a handle removably attached to the base. The handle includes a bottom plate; a rod that extends vertically from the bottom plate, and a grip portion that is configured to connect to a locking means formed in a top portion of the rod.

In another embodiment, an apparatus for measuring lifting capacity includes a container having an open top, opposed parallel side walls, a front wall, a back wall, and a base extending between the walls which defines an open space between the walls, and a handle that extends between the opposed side walls. A thickness of one of the back wall or the front wall is greater than the thickness of the other of the back wall or the front wall such that the open space is off-center. The handle is centered over the open space.

In still another embodiment, an apparatus for measuring lifting capacity has a container having an open top, opposed parallel side walls, a front wall, a back wall, and a base extending between the walls defining an open space therein. A handle is removably attached to the base and includes a bottom plate; a rod extending vertically from the bottom plate, wherein a top portion of the rod has a void formed therein, the void comprising a first portion having a first diameter and a second portion having a second diameter, the second diameter being smaller than the first diameter; and a grip portion. The grip portion has a grip secured to a grip base, and the grip base is fastened to an extension member. The first portion of the rod has a locking means formed therein, and a spring is received into the second portion. The grip portion extension member is received into the first portion such that the extension member rests atop the spring such that in an initial position, the spring biases the grip portion away from the rod; and in a second position, the grip portion engages with the locking means such that the spring is compressed.

BRIEF DESCRIPTION OF THE DRAWINGS

FIG. 8A is a front perspective view of a spring load assembly which is received by the rod of FIG. 7A.

FIG. 8B is a front view of the spring load assembly of FIG. 8A.

FIG. 8C is a front view of a spring load shaft of the spring load assembly of FIG. 8A showing a threaded hole in hidden lines.

FIG. 8D is a front view of a threaded screw received by the spring load shaft of FIG. 8C.

FIG. 8E is a top view of a washer incorporated into the spring load assembly of FIG. 8A.

FIG. 8F is a front view of a spring of the spring load assembly of FIG. 8A.

FIG. 15B is a side view of an extension member of the grip portion of FIG. 9A.

FIG. 15C is a top view of the extension member of FIG. 15B.

FIG. 17 is a section view of the crate of FIG. 16A.

FIG. 18 is a top view of the crate of FIG. 16A.

WRITTEN DESCRIPTION

Figure 1:
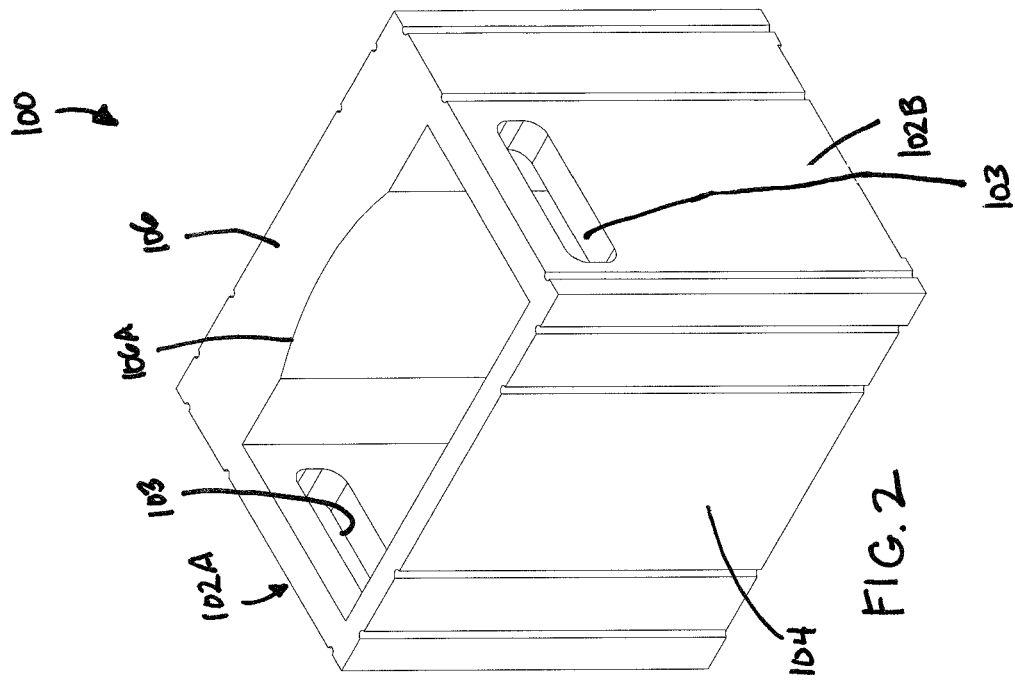
FIG. 1 is a right perspective view of a lifting crate according to one embodiment of the invention.

Embodiments of apparatus for measuring lifting capacity and methods of use are disclosed herein. With reference to FIGS. 1-5, in one embodiment, an apparatus for measuring lifting capacity includes a lifting crate 100 having opposing side walls 102A and 102B, a front face 104, a back face 106, and a base 110 defining a void 108 therein. The top of the crate 100 may be open.

Respective apertures 103 may be molded into the opposing side walls 102A and 102B thus forming a first set of handles for lifting the crate 100. For ease of lifting, the apertures 103 may be positioned substantially towards a top edge of the crate 100.

Figure 3:
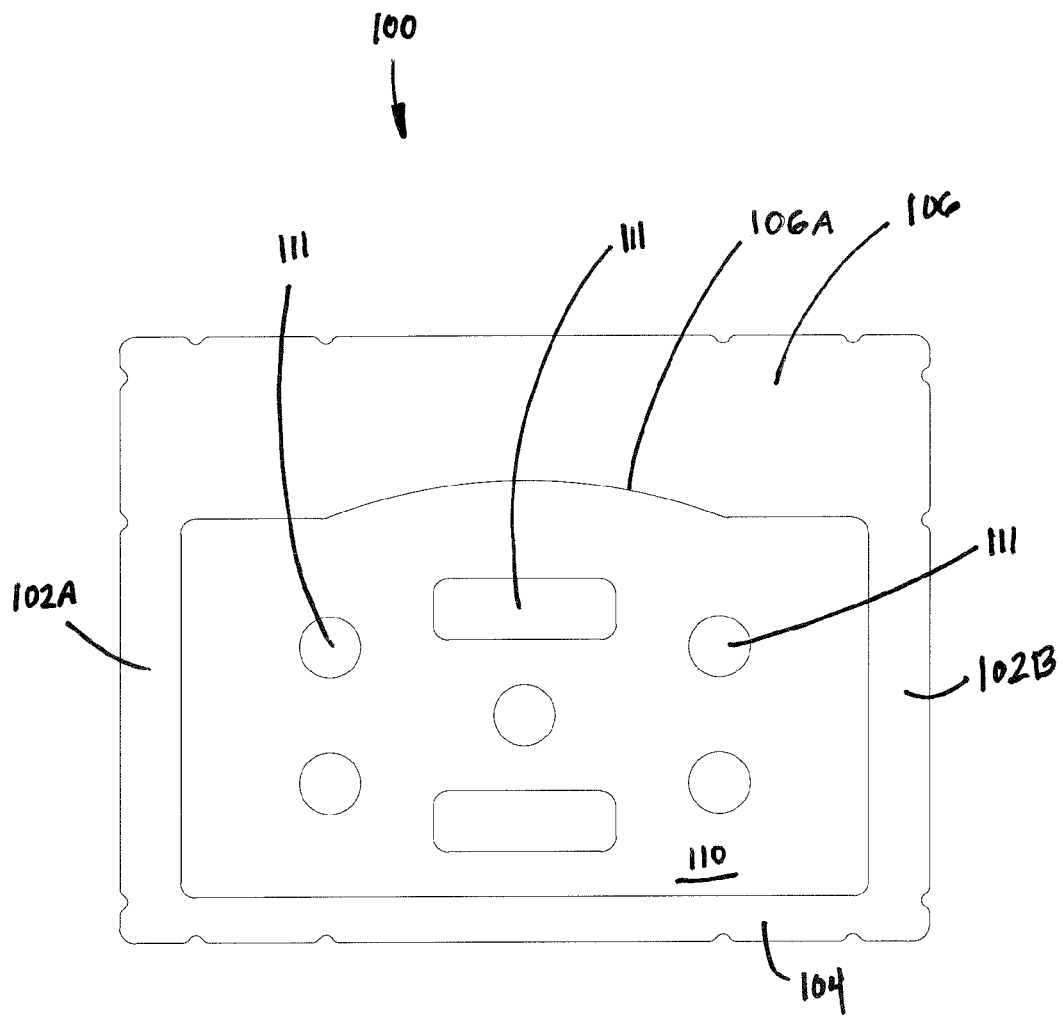
FIG. 3 is a top view of the lifting crate of FIG. 1.
Figure 4:
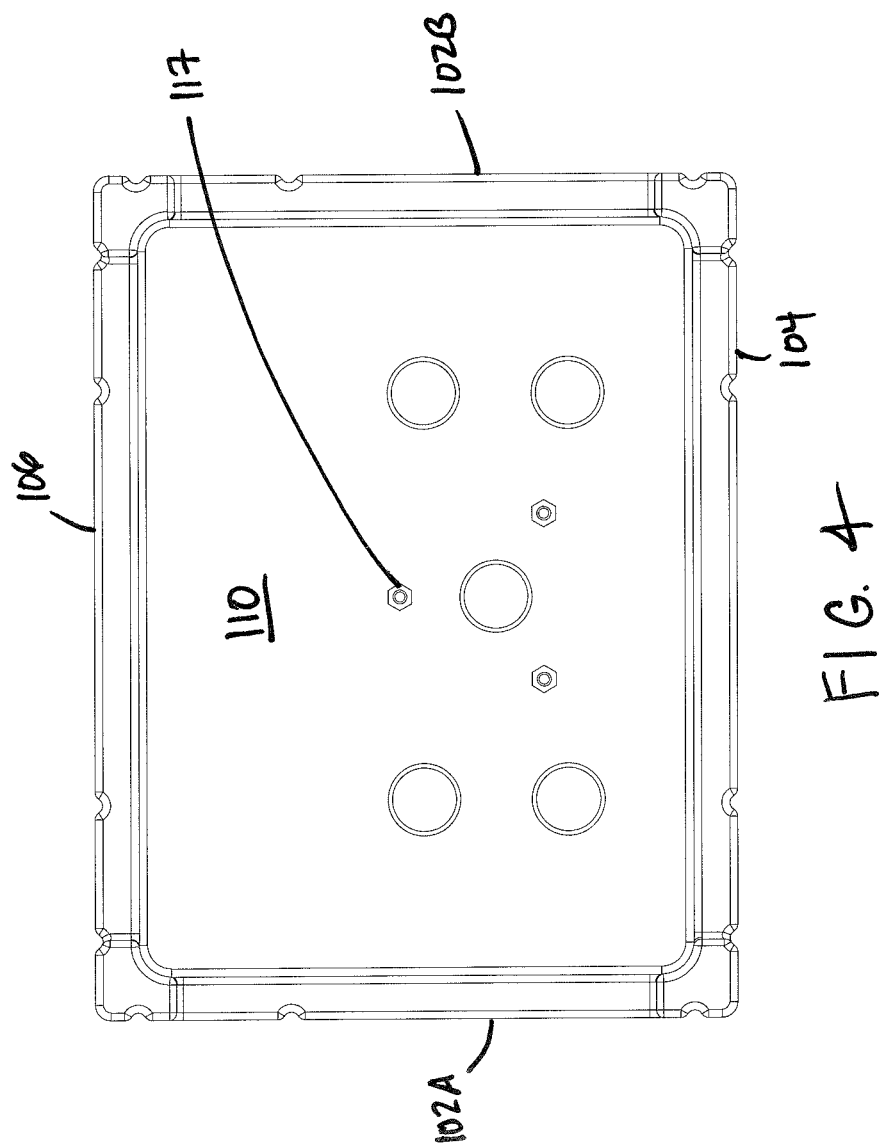
FIG. 4 is a bottom view of the lifting crate of FIG. 1.
Figure 5:
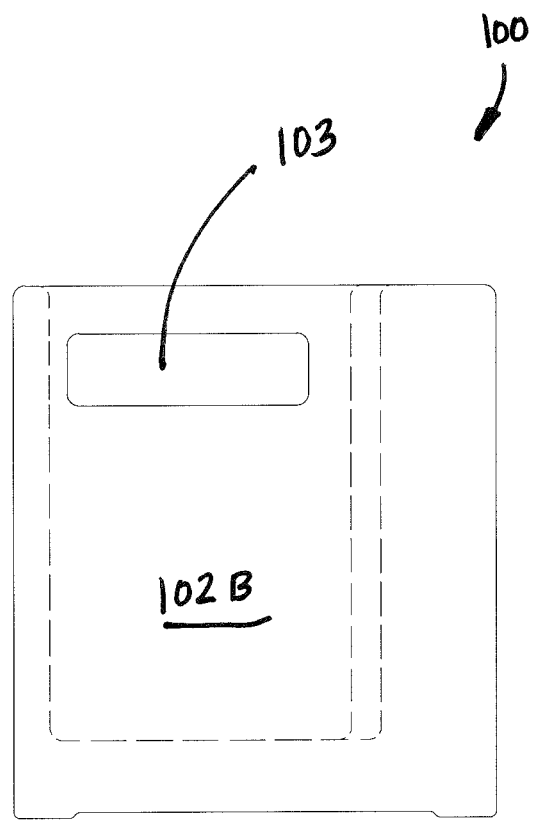
FIG. 5 is a left side view of the lifting crate of FIG. 1.

The crate base 110 may be substantially flat and have a plurality of openings 111 formed therein. The openings 111 may come in a variety of shapes, for example, circular or rectangular as shown in FIG. 3. The openings 111 may provide additional strength to the bottom of the crate. Additional apertures (shown in FIG. 4) may be included in the base 110 for receiving bottom plate attachments 117 as described below.

Figure 6A:
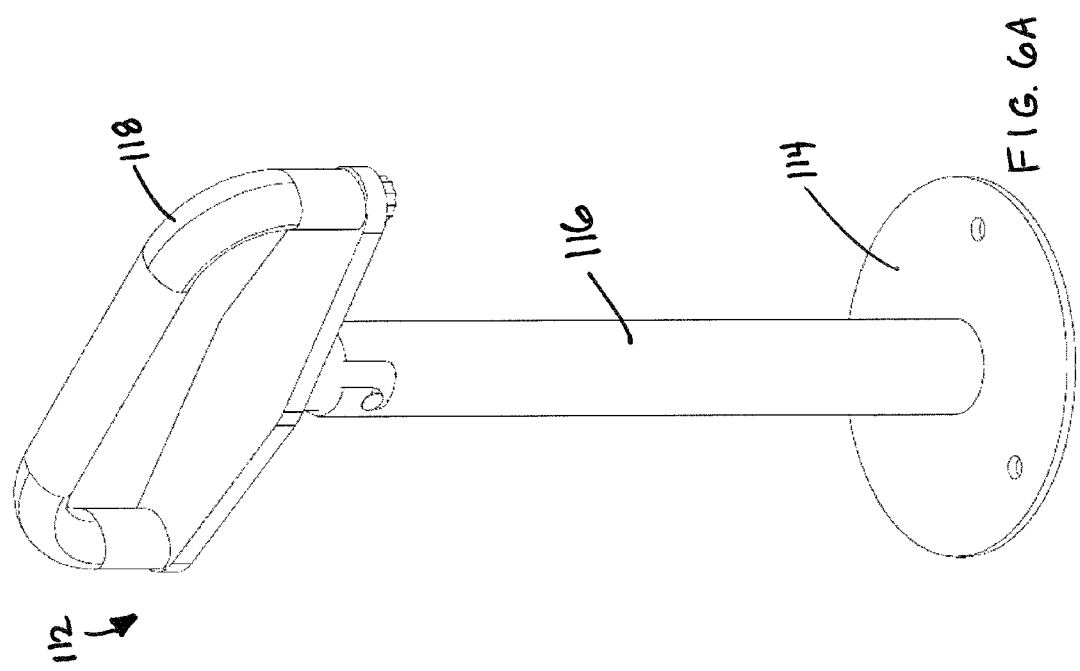
FIG. 6A is a top perspective view of an embodiment of a handle configured to attached to the crate of FIG. 1.
Figure 6B:
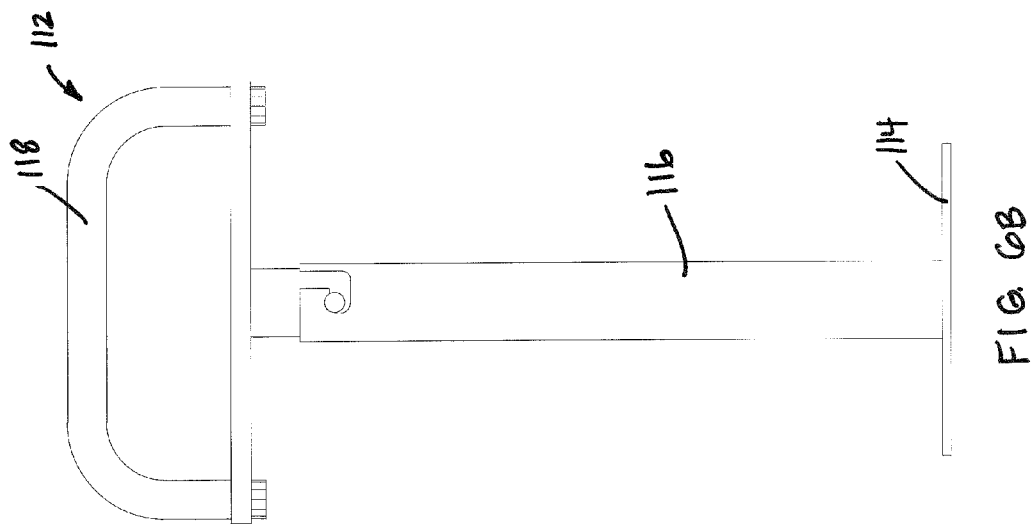
FIG. 6B is a front view of the handle of FIG. 6A.
Figure 7A:
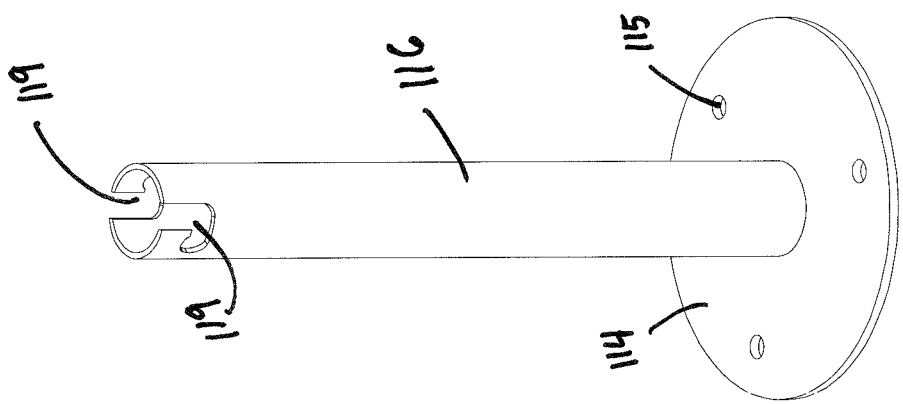
FIG. 7A is a top perspective view of a rod portion and bottom plate of the handle of FIG. 6A.
Figure 7C:
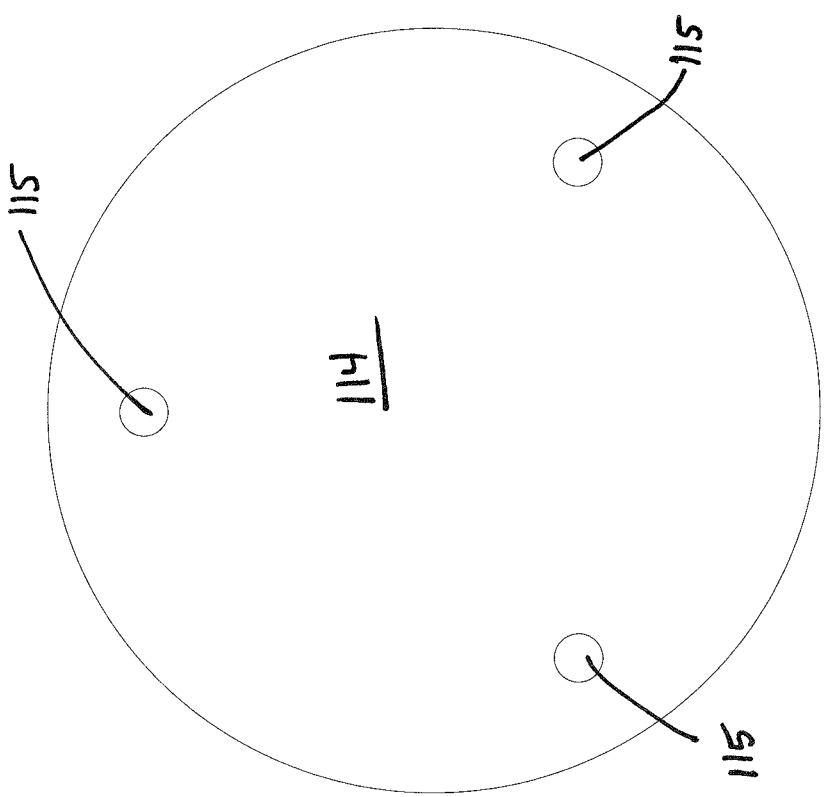
FIG. 7C is a bottom view of the bottom plate.
Figure 7F:
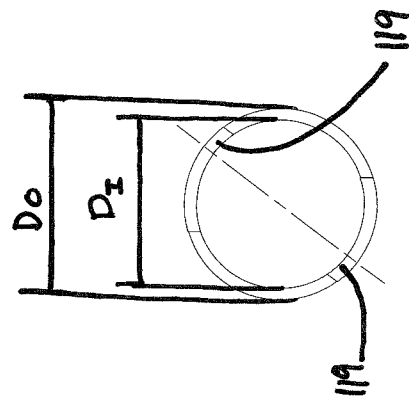
FIG. 7F is a close-up top view of the rod portion of FIG. 7A.
Figure 7E:
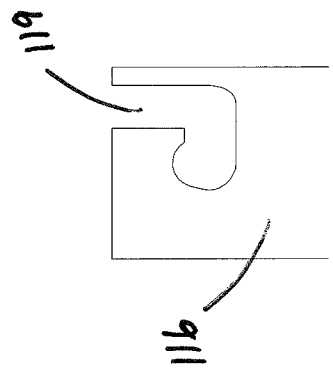
FIG. 7E is a close-up side view of the top of the rod portion of FIG. 7A showing locking means.
Figure 7B:
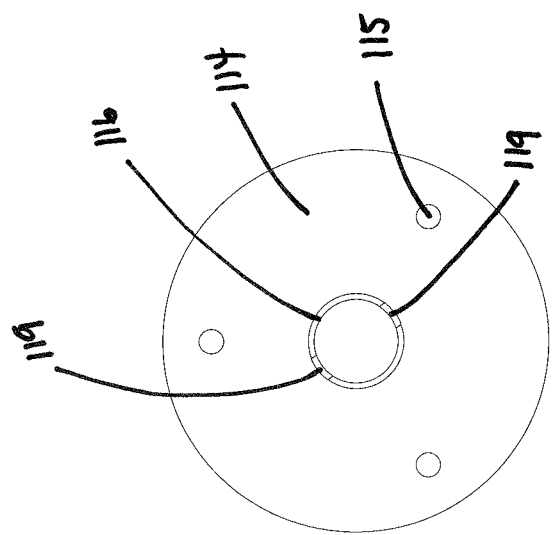
FIG. 7B is a top view of the rod portion and bottom plate of FIG. 7A.
Figure 7D:
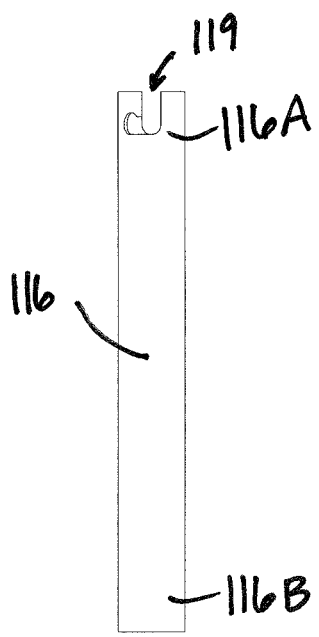
FIG. 7D is a side perspective view of the rod portion of FIG. 7A.

A handle 112, which may generally include a bottom plate 114, a rod 116, and a grip portion 118, is illustrated in FIGS. 6A and 6B. The handle 112 may be releasably attached to the base 110 of the crate 100 via base plate 114. Referring now to FIGS. 7B and 7C, the bottom plate 114 may have a plurality of apertures 115 which may correspond with the apertures in the base. The bottom plate attachments 117 (FIG. 4) are received into the corresponding apertures in the base 110 and the bottom plate 114 to secure the handle 112 to the crate 100. The bottom plate attachments 117 may include any acceptable mechanical fastening mechanism, such as a nut and bolt, rivet, screw, clevis pin, etc. It may be understood by those in the art that it is desirable for the handle 112 to be firmly attached to the base 110 such that it does not move around when the handle 112 is used to lift the crate 100.

Referring now to FIGS. 7A, 7D, 7E, and 7F, the rod 116 may consist of a hollow tubular member having an inner diameter $D_I$ and an outer diameter $D_O$. A bottom rim 116B of the rod 116 may be attached to the bottom plate 114 through welding, chemical attachment, mechanical attachment, etc. A top rim 116A of the rod 116 may include a locking mechanism 119 for attaching the grip portion 118 to the rod 116. The locking mechanism 119 may be, for example, a cutout in the top rim 116A of the rod resembling an "L" (or a backwards "L"). The horizontal portion of the "L" may end in a slightly upward direction (see, e.g., FIG. 7E) such that the grip portion 118 is maintained in connection with the rod 116 as described in greater detail below.

Moving on, FIGS. 8A-8F illustrate a spring load assembly 120. The spring load assembly 120 may include a spring load shaft 122 having a threaded hole 123, a screw 124, a washer 125, and a spring 126. The screw 124 may have a threaded end 124A and a cap 124B. The washer 125 and the spring 126 may be slid onto the screw 124 such that the washer 125 is closer to the cap 124B, and the threaded end 124A of the screw 124 may be received into the threaded hole 123 of the spring load shaft 122. As described below, the spring load assembly 120 may aid in the connection of the grip portion 118 with the rod 116.

Figure 9A:
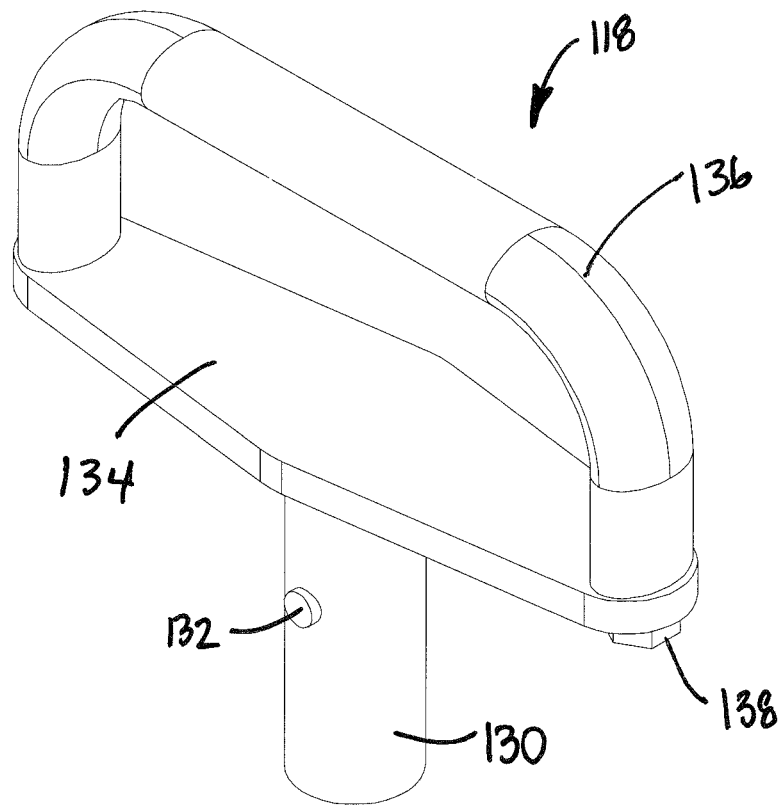
FIG. 9A is a side perspective view of a grip portion of the handle of FIG. 6A.
Figure 9B:
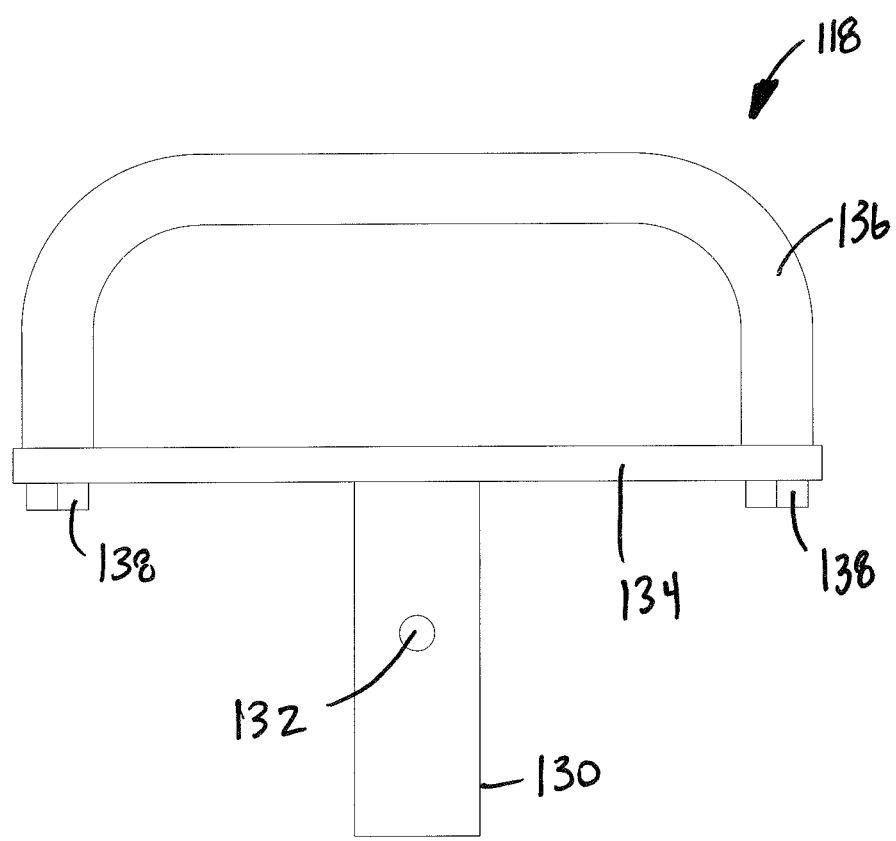
FIG. 9B is a front view of the grip portion of FIG. 9A.
Figure 9C:
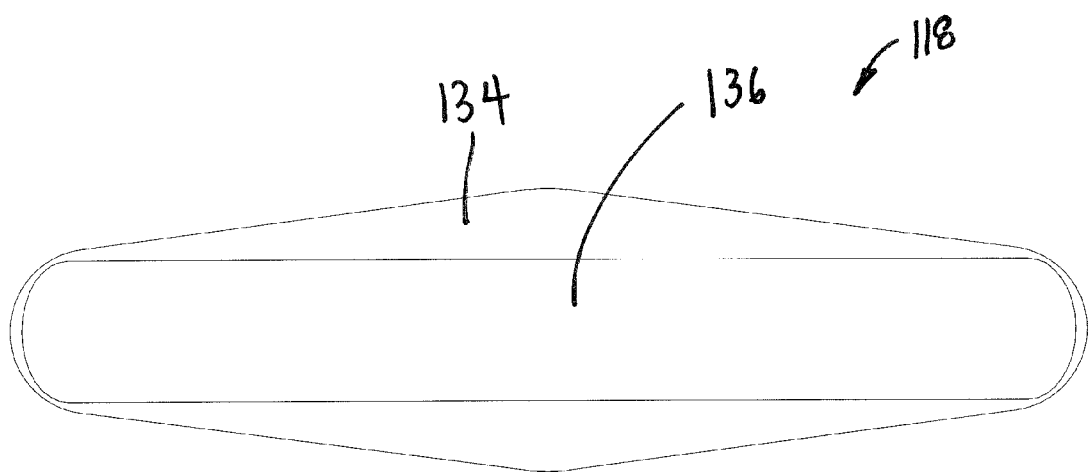
FIG. 9C is a top view of the grip portion of FIG. 9A.
Figure 9D:
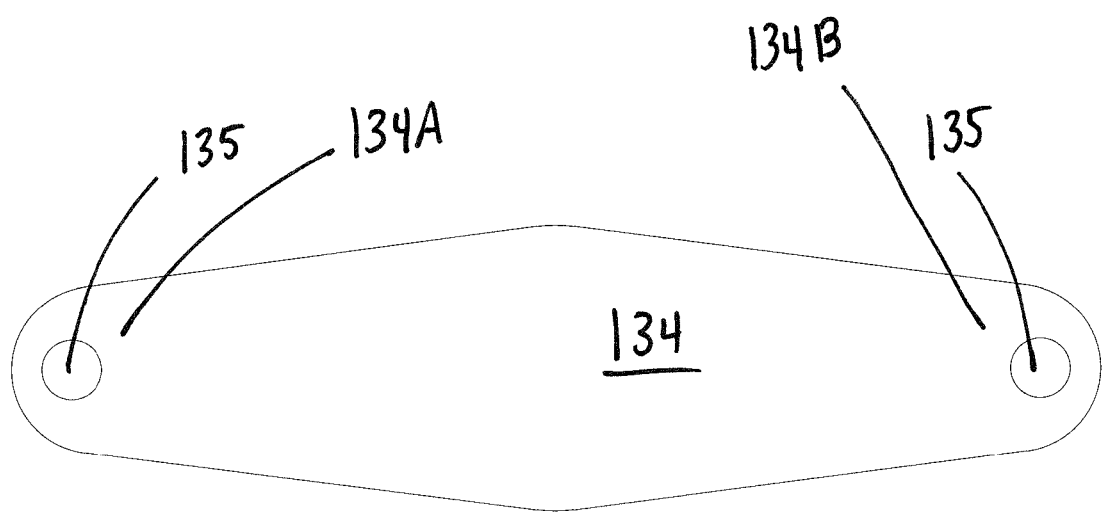
FIG. 9D is a top view of a grip base of the grip portion of FIG. 9A.

The grip portion 118, illustrated in FIGS. 9A, 9B, and 9C includes an extension member 130, a pin 132, a grip base 134, and a grip 136. The extension member 130 may be a hollow tube, and may include a hole 131 (see, e.g., FIGS. 9F and 9G) extending perpendicularly there through for receiving the pin 132 (FIG. 9H). The extension member 130 is attached to the grip base 134 through welding, chemical attachment, mechanical attachment, etc. The grip base 134 may be a substantially flat oblong member having opposed ends 134A and 134B (FIG. 9D). Respective openings 135 may be formed in the opposed ends 134A and 134B for receiving mechanical attachments 138 for securing the grip 136 to the grip base 134.

Figure 9E:
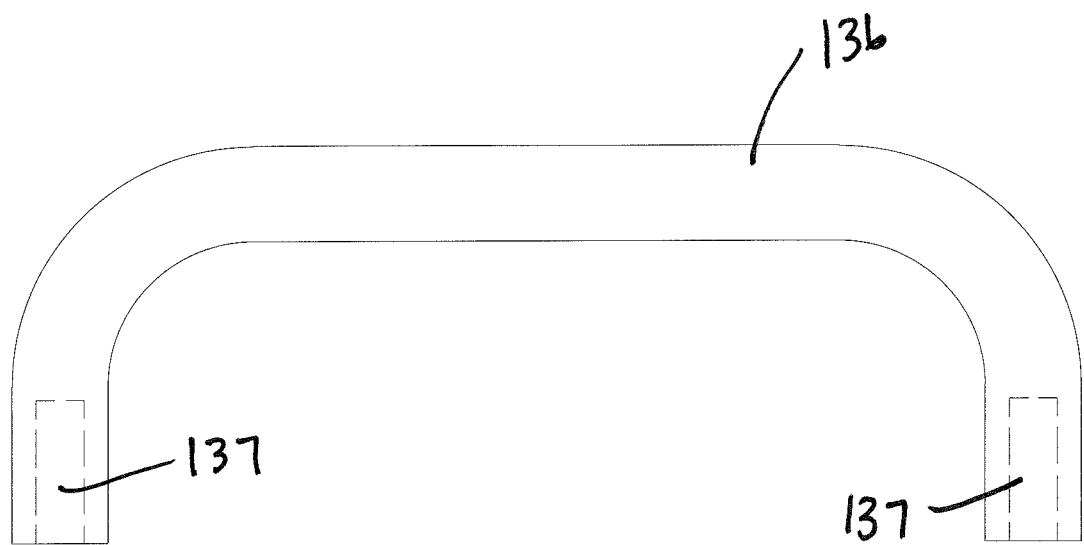
FIG. 9E is a side view of a grip of the grip portion of FIG. 9A showing threaded holes in hidden lines.
Figure 9F:
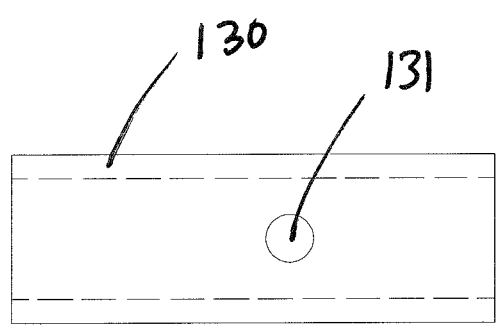
FIG. 9F is a side view of an extension member of the grip portion of FIG. 9A.
Figure 9G:
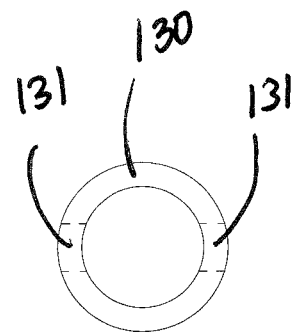
FIG. 9G is a top view of the extension member of FIG. 9F.
Figure 9H:
FIG. 9H is a side view of a pin of the extension member of FIG. 9F.

As shown in FIG. 9E, the grip 136 may be, for example, a tubular member having an inverted "U" configuration, although other configurations may also be possible. Opposed ends 136A and 136B of the grip 136 may have threaded holes 137 formed therein for receiving the mechanical attachments 138. The mechanical attachments may be any acceptable such attachment, including but not limited to threaded screws. The threaded holes 137 in the grip 136 may be matched up with the openings 135 in the grip base 138 and the mechanical attachments 138 may be inserted from the bottom side of the base 138 through the openings 135 and received by the threaded holes 137.

As is briefly described above, the spring load assembly 120 may be configured to fit inside the hollow rod 116 to aid in securing the grip portion 118 to the locking mechanism 119 of the rod 116. When the grip portion 118 is not attached to the rod 116, the spring 126 in the spring load assembly 120 is uncompressed and the washer 125 is substantially adjacent the screw cap 124B (FIGS. 8A and 8B).

Figure 8G:
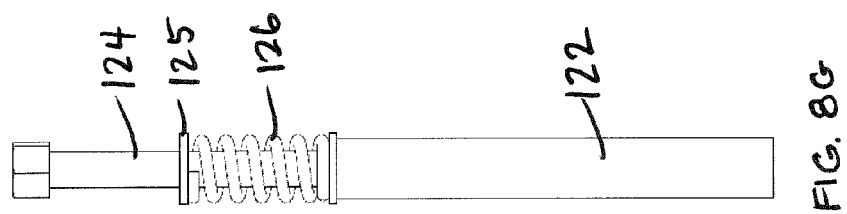
FIG. 8G is a front view of the spring load assembly of FIG. 8A in a compressed position.
Figure 10:
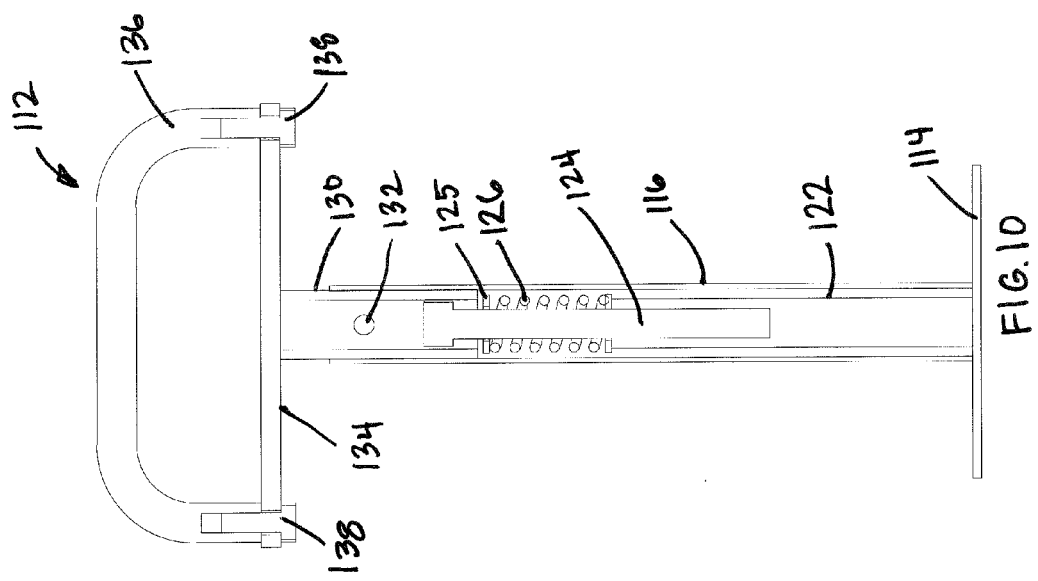
FIG. 10 is a section view of the handle of FIG. 6A showing the internal components of the handle.

To attach the grip portion 118 to the rod 116, the grip portion 118 is positioned over the rod 116 having the spring load assembly 120 therein such that the bottom of the extension member 130 touches the washer 125 and the screw cap 124B is received into the hollow center of the extension member 130. The grip portion 118 may be rotated such that the pin 132 is generally lined up with the locking means 119. The grip portion 118 may then be pushed in a downward direction towards the rod 116 such that the pin 132 engages with the locking means 119, and in particular, the upwardly extending portion of the horizontal section of the "L". The downward pressure on the spring 126 causes the spring 126 to become compressed (FIG. 8G). Once the pin 132 is engaged with the locking means 119, the spring 126 biases the grip portion 118 upwards so that the pin 132 is maintained in secure connection with the locking means 119. FIG. 10 shows a section view of the grip portion 118 engaged with the spring load assembly 120, which is housed inside the rod 116.

Alternate handles may be desirable, and may optionally be additionally provided for use with the crate 100. FIGS. 11-15 illustrate another embodiment of a handle 212 that is substantially similar to handle 112 except as shown and described herein, or as would be inherent. Further, those skilled in the art will appreciate that the embodiment 212 may be modified in various ways, such as through incorporating all or part of any of the various described embodiments, for example. For uniformity and brevity, reference numbers between 200 and 299 may be used to indicate parts corresponding to those discussed above numbered between 100 and 199 (e.g., grip portion 118 corresponds generally to the grip portion 118), though with any noted or shown deviations.

Figure 11A:
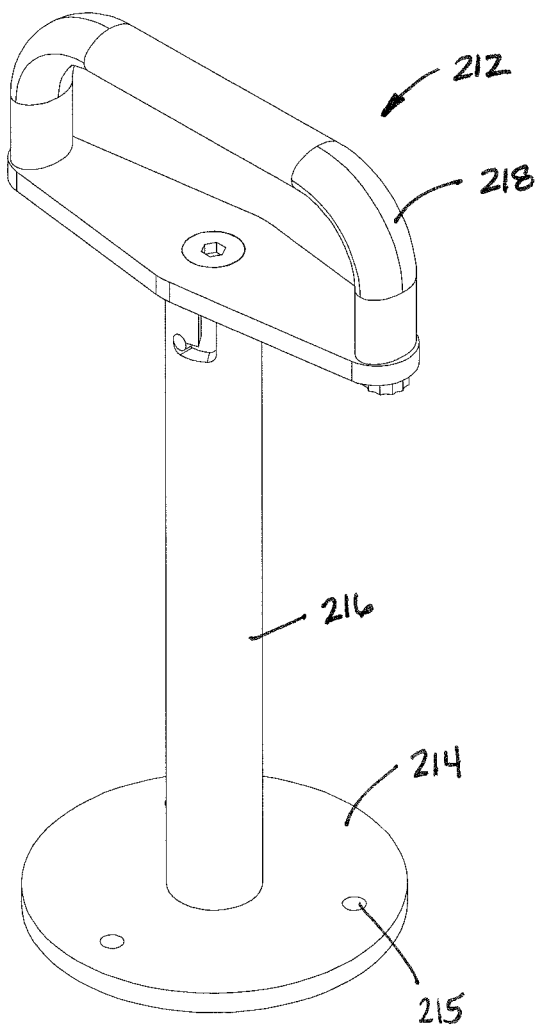
FIG. 11A is a perspective view of another embodiment of a handle configured to attach to the crate of FIG. 1.
Figure 11B:
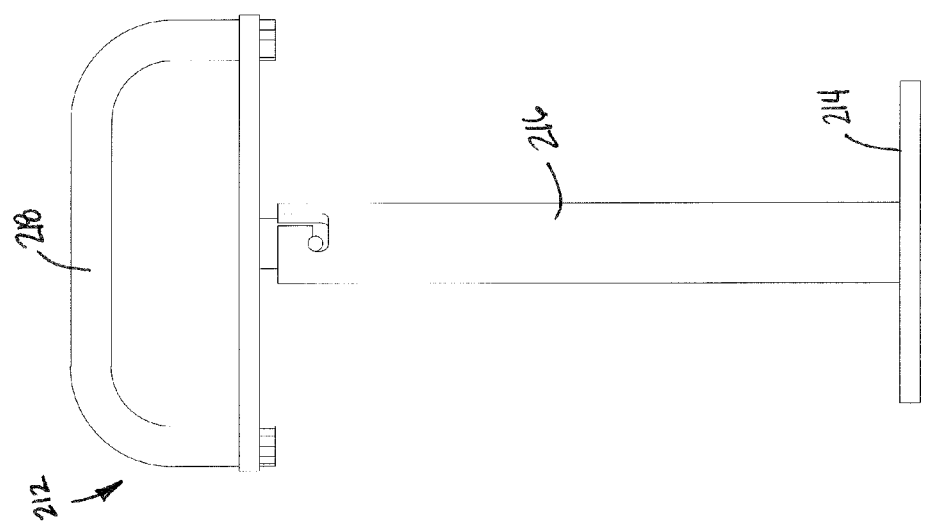
FIG. 11B is a front view of the handle of FIG. 11A.
Figure 13:
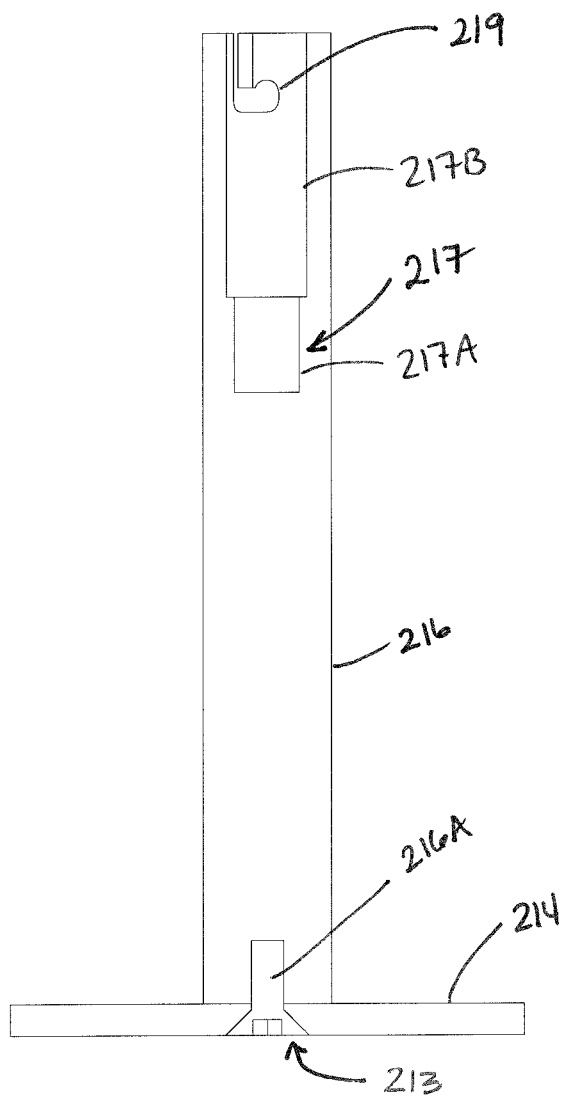
FIG. 13 is a sectional view of a rod portion and bottom plate of the handle of FIG. 11A.

As shown in FIGS. 11A and 11B, the handle 212 includes a bottom plate 214, a rod 216, and a grip portion 218. The bottom plate 214 may be substantially similar to bottom plate 114, and may include a plurality of apertures 215. As shown in FIG. 13, the bottom plate 214 may further include an aperture 213 for receiving a mechanical fastener such as a countersunk head screw, bolt, rivet, et cetera for attaching the bottom plate 214 to the rod 216. The rod 216 may have a corresponding cavity 216A for receiving the mechanical fastener. The cavity may be threaded to engage with the mechanical fastener.

Figure 12:
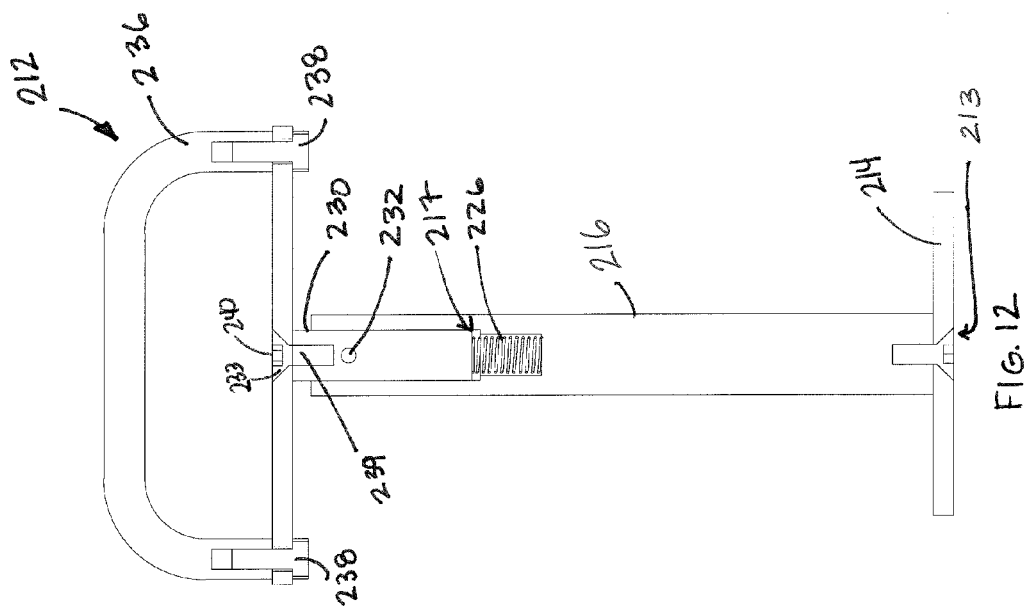
FIG. 12 is a sectional view of the handle of FIG. 11A.

An end of the rod 216 opposite the cavity 216A may be equipped with a void 217 for receiving a spring 226 and the respective grip portion extension member 230 as shown in FIG. 12. The void 217 may have a first portion 217A having a first diameter and a second portion 217B having a second diameter. The first diameter may be smaller than the second diameter, and configured to receive the spring 226. In a naturally expanded position, the spring 226 may extend past a top edge of the first portion 217A to contact a bottom face of the extension member 230. When the handle 212 is installed onto the rod 216, the spring 226 is compressed such that the pin 232 engages with the locking mechanism 219 of the rod 216 as described above regarding the rod 116 and handle 116.

Figure 14:
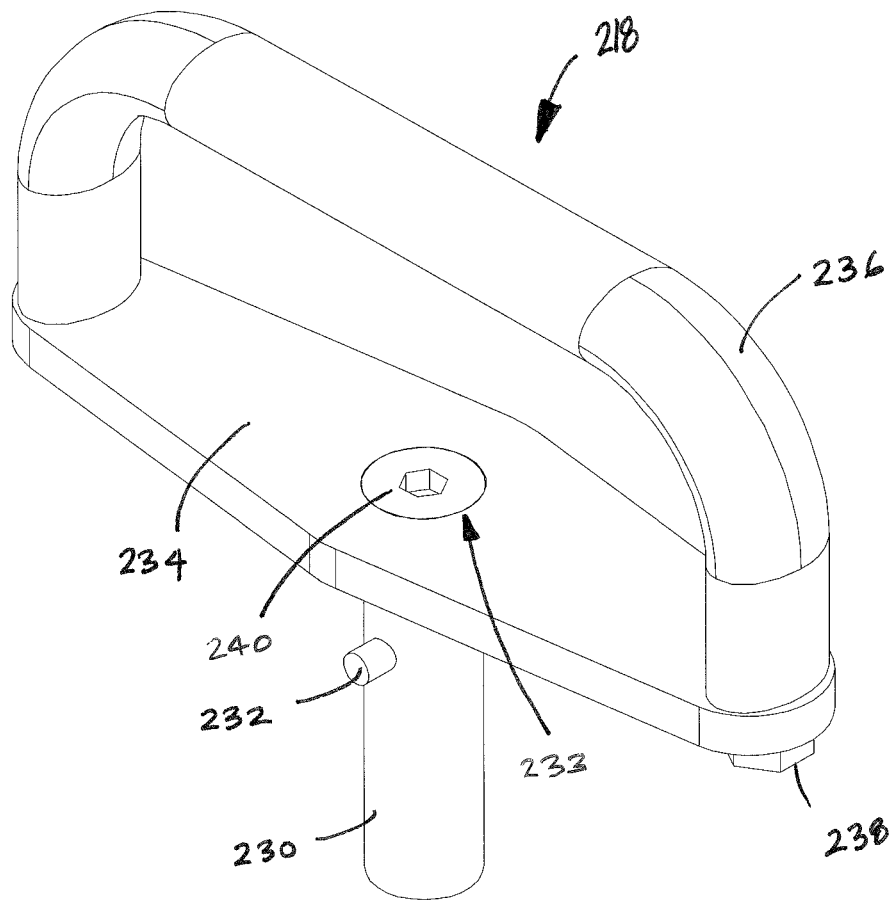
FIG. 14 is a perspective view of the grip portion of the handle of FIG. 11A.
Figure 15A:
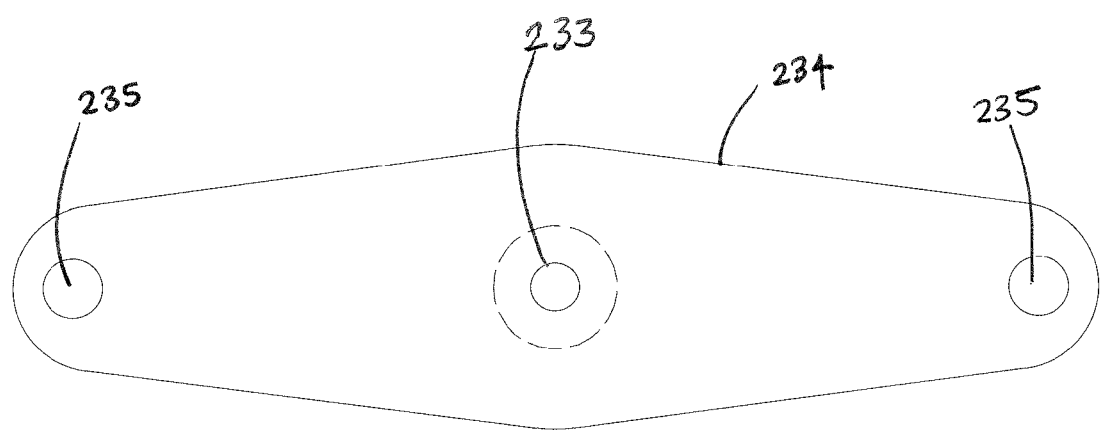
FIG. 15A is a top view of a grip base of the grip portion of the handle of FIG. 11A.
Figure 16B:
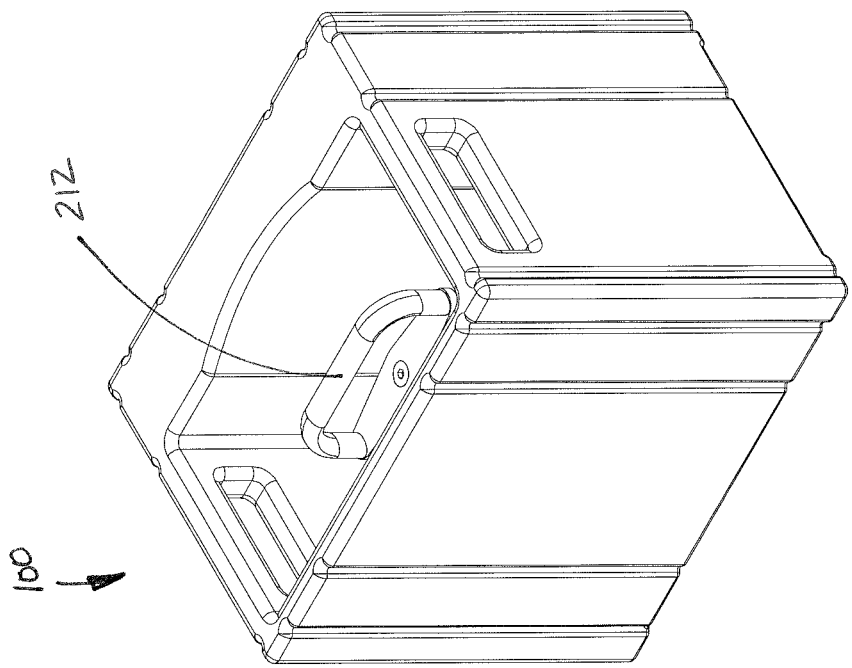
FIG. 16B is a left perspective view of the crate of FIG. 16A.
Figure 16A:
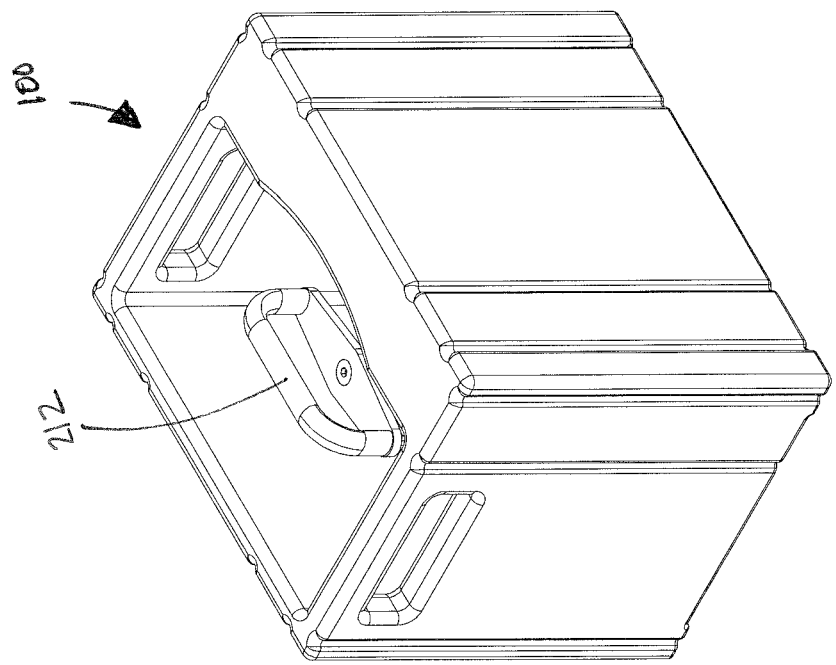
FIG. 16A is a right perspective view of the crate of FIG. 1 showing a handle installed therein.

Referring now to FIG. 14, the handle 218 includes a grip portion 236 attached to a grip base 234. The grip base 234 may be substantially similar to the grip portion 136, and may include a plurality of apertures 235 for receiving fasteners 238 for connecting the grip base 234 to the grip portion 236. The grip base 234 may additionally have a cavity 233 for receiving a mechanical fastener 240 such as a countersunk head screw, bolt, rivet, et cetera for attaching the grip base 234 to the extension member 230. Accordingly, the extension member 230 may have a corresponding void 239 for receiving the fastener 240 (FIGS. 15B and 15C). The void 239 may be threaded to receive fastener 240.

Another alternate handle may include a tubular member having ends plates at opposing ends. The end plates may be configured to attach to sides of the crate 100, such as opposing sides 102A and 102B via, for example, mechanical fasteners such as screws, rivets, or the like, or other attachment means. The opposing sides 102A and 102B may thus be configured to receive the mechanical fasteners, including having holes (threaded or otherwise) formed therein.

FIGS. 16A, 16B, 17, and 18 illustrate a crate 100 having a handle (in this case, handle 218) installed therein. The handle 218 may be generally centered over the weight of the crate 100. Centering the handle 218 over the weight may allow the create 100 to remain substantially upright when lifted by one hand of a subject. Additionally, the handle 218 may be attached to the crate base 110 at an off-center position closer to either the front face 104 or the back face 106 of the crate 100 allowing the crate 100 to be comfortably gripped near the body of the subject. In order to accommodate the off-center position of the handle 218, either the back face 108 or the front face 106 of the crate 100 may be wider than the opposite face and the opposing sides 102A and 102B.

In some methods of use, it may be beneficial to alternate the handles used to lift the crate, which may allow for a more total evaluation of the subject. Accordingly, a first set of measurements may be taken without any handles such that the subject lifts the crate 100 using the apertures 103 formed in the opposing sides 102A and 102B. After that, the handle 118 may be secured to the crate 100 as described above. Subsequently, a second set of measurements may be taken as the subject lifts the crate 100 using the handle 118. A third set of measurements may be taken by substituting the handle 118 with an alternate handle (such as thosedescribed immediately above).

Figure 2:
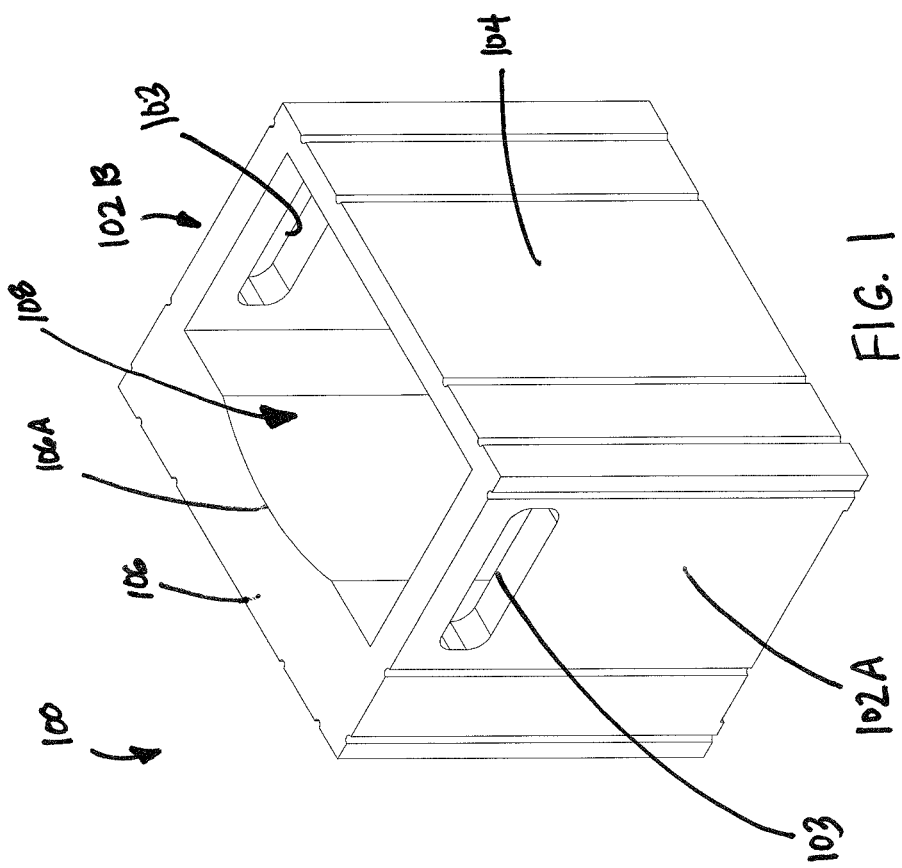
FIG. 2 is a left perspective view of the lifting crate of FIG. 1.

In some embodiments, it may be desirable to modify the weight of the crate 100. Measurements may be recorded for the subject for different crate weights, e.g., without weights, with additional 5 pound weight, with additional 10 pound weights, etc. As shown in FIGS. 1-3, a portion of the back face 106 of the crate 100 (e.g., a substantially center portion) may be shaped into an arc 106A. Free weights (for example, circular plate weights or bow-tie shaped weights) may be received into the void 108 of the crate 100, the arc 106A allowing the weights to be more easily removed from the void 108.

In embodiments where handle 118 is used, to prevent the weights from moving around while the crate 100 is lifted, it may be desirable (though not required) to select weights that may be placed onto the rod 116. In such a case, the grip portion 118 may be removed from the rod 116 as described above. The free weight(s) may then be positioned on the rod 116 and into the void 108. The grip portion 118 may then be re-engaged with the rod 116.

The crate 100 may be formed of any material, such as wood, molded plastic, metal, et cetera. As the initial weight of the crate 100 contributes to the overall weight being lifted by the subject, the material chosen for the crate 100 may be chosen based on the impact that it will have on the weight of the system. For example, if it is desired for the crate 100 to have a heavier starting weight, the crate 100 may be formed of, for example, wood or metal. Alternately, if it is desired for the crate 100 to have a lighter starting weight, then the crate 100 may be formed of, for example, molded plastic. Additionally, the crate 100 may be manufactured in a variety of sizes which may be useful for testing the lifting capacity of individuals having different needs (e.g., children versus adults).

The crate 100 may be used in combination with other apparatus for evaluating lifting capacity so that the evaluator may determine the consistency with which the subject lifts between the various apparatus. For example, U.S. Pat. No. 6,216,535 to Schapmire describes an apparatus for testing isoinertial lifting capacity. The apparatus described in the '535 Patent may assess lifting force of a subject by mimicking the mechanics of lifting a box of weights. Therefore, the subject's lifting capacity as measured by the device of the '535 Patent should translate to the subject's lifting capacity of the crate. If the subject does not perform equally using both the device of the '535 Patent (or any other device) and the device of the present invention, it may suggest that the subject is not putting forth sufficient effort on one or more of the tests, which may require additional testing. A person evaluating the results of the tests may reach conclusions about the subject's performance on the various tests, including the validity of the subject's lifting efforts and the subject's maximum lifting capacity.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

Further, it will be understood that certain features and subcombinations are of utility and may be employed without reference to other features and subcombinations and are contemplated within the scope of the disclosure. Further, various steps set forth herein may be carried out in orders that differ from those set forth herein without departing from the scope of the present methods. This description shall not be restricted to the above embodiments.

The invention claimed is:

1. An apparatus for measuring lifting capacity, comprising:
   a container having an open top, opposed parallel side walls, a front wall, a back wall, and a base extending between the walls defining an open space therein; and
   a handle removably attached to the base, comprising:
   a bottom plate;
   a rod extending vertically from the bottom plate, a top portion of the rod having a locking means formed therein; and
   a grip portion configured to connect to the rod via the locking means;
   wherein the rod has an outer diameter and an inner diameter, a space being formed within the inner diameter for receiving a spring load assembly comprising:
   a screw having a threaded end and a cap opposite the threaded end;
   a washer and a spring positioned around the screw such that the washer is between the cap and the spring; and
   a spring load shaft having a threaded hole therein for receiving the screw; and
   wherein:
   in an initial position the spring is expanded thus biasing the washer toward the cap; and
   in a compressed position, the washer is biased away from the cap.

2. The apparatus of claim 1, wherein the handle grip portion comprises:
   a grip fastened to a grip base; and
   an extension member extending vertically from the grip base and having a pin inserted perpendicularly there through, wherein the pin engages with the locking means in the handle rod.

3. The apparatus of claim 2, wherein the bottom plate has a plurality of apertures formed therein which correspond to a plurality of apertures formed in the container base, and wherein the respective apertures are configured to receive attachment members for securing the bottom plate to the container base.

4. The apparatus of claim 3, wherein corresponding apertures are formed into the opposing sides walls of the container.

5. The apparatus of claim 4, wherein the handle is attached to the base such that it is closer to one of the front side or the back side of the container.

6. The apparatus of claim 5, wherein the rod receives weights for increasing the weight of the container, and wherein the back side of the container has an arced configuration generally corresponding to the shape of the weights.

7. An apparatus for measuring lifting capacity comprising:
   a container having an open top, opposed parallel side walls, a front wall, a back wall, and a base extending between the walls defining an open space therein; and
   a handle extending between the opposed side walls, the handle having a rod for receiving a spring load assembly, the spring load assembly comprising:
   a screw having a threaded end and a cap opposite the threaded end;
   a washer and a spring positioned around the screw such that the washer is between the cap and the spring; and
   a spring load shaft having a threaded hole therein for receiving the screw:
   wherein:
   a thickness of one of the back wall and the front wall is greater than the thickness of the other of the back wall and the front wall such that the open space is off-center; and
   the handle is centered over the open space.

8. The apparatus of claim 7, wherein at least one weight is receivable into the open space, and wherein the back wall of the apparatus has a shape corresponding to the shape of the weight.

9. The apparatus of claim 8, wherein corresponding apertures are formed into the opposing sides walls of the container.

10. The crate of claim 9, wherein the container is one of molded plastic and metal.

11. An apparatus for measuring lifting capacity, comprising:
    a container having an open top, opposed parallel side walls, a front wall, a back wall, and a base extending between the walls defining an open space therein; and
    a handle removably attached to the base, comprising:
    a bottom plate;
    a rod extending vertically from the bottom plate, wherein a top portion of the rod has a void formed therein, the void comprising a first portion having a first diameter and a second portion having a second diameter, the second diameter being smaller than the first diameter; and
    a grip portion, comprising:
    a grip secured to a grip base, the grip base being fastened to an extension member;
    wherein:
    the first portion has a locking means formed therein;
    a spring load assembly is received into the second portion, the spring load assembly comprising:
    a screw having a threaded end and a cap opposite the threaded end;
    a washer and a spring positioned around the screw such that the washer is between the cap and the spring; and
    a spring load shaft having a threaded hole therein for receiving the screw and washer;
    the grip portion extension member is received into the first portion such that the extension member rests atop the spring;
    in an initial position, the spring biases the grip portion away from the rod; and
    in a second position, the grip portion engages with the locking means such that the spring is compressed.

12. The apparatus of claim 11, wherein the extension member has a pin inserted therethrough, wherein the pin engages with the locking means in the handle rod.

13. The apparatus of claim 12, wherein the bottom plate has a plurality of apertures formed therein for securing the handle to the container base.

14. The apparatus of claim 13, wherein the locking means has a generally "L" shape configuration.

15. The apparatus of claim 14, wherein corresponding apertures are formed into the opposing sides walls of the container.

16. The apparatus of claim 15, wherein the handle is attached to the base such that it is closer to one of the front side or the back side of the container.

17. The apparatus of claim 16, wherein the rod receives weights for increasing the weight of the container, and wherein the back side of the container has an arced configuration generally corresponding to the shape of the weights.

18. The apparatus of claim 17, wherein the grip has a generally inverted "U" shaped configuration.

19. The apparatus of claim 18, wherein the container is one of molded plastic and metal.

* * * * *